(12) United States Patent
Snyder

(10) Patent No.: US 10,434,261 B2
(45) Date of Patent: Oct. 8, 2019

(54) DRUG PELLET DELIVERY SYSTEM AND METHOD

(71) Applicant: Warsaw Orthopedic, Inc., Warsaw, IN (US)

(72) Inventor: Lloyd M. Snyder, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 42 days.

(21) Appl. No.: 15/345,764

(22) Filed: Nov. 8, 2016

(65) Prior Publication Data

US 2018/0126090 A1 May 10, 2018

(51) Int. Cl.
*A61M 5/315* (2006.01)
*A61K 9/00* (2006.01)
*A61M 37/00* (2006.01)

(52) U.S. Cl.
CPC ....... *A61M 5/31566* (2013.01); *A61K 9/0024* (2013.01); *A61M 5/315* (2013.01); *A61M 37/0069* (2013.01)

(58) Field of Classification Search
CPC .......... A61M 37/0069; A61M 5/31566; A61M 5/315; A61M 5/31501; A61M 5/31505; A61M 5/31565; A61M 2005/31506; A61M 31/00; A61M 31/007; A61M 37/00; A61B 2090/3987; A61B 17/3468; A61B 2017/00969; A61N 5/1007; A61N 2005/101; A61N 2005/1012; A61D 7/00
See application file for complete search history.

(56) References Cited

U.S. PATENT DOCUMENTS

| | | | |
|---|---|---|---|
| 1,881,854 A | 10/1932 | Muir | |
| 3,520,299 A | 7/1970 | Tapper et al. | |
| 4,105,030 A | 8/1978 | Kercso | |
| 4,164,560 A | 8/1979 | Folkman et al. | |
| 4,344,431 A | 8/1982 | Yolles | |
| 4,346,709 A | 8/1982 | Schmitt | |
| 4,427,015 A | 1/1984 | Redeaux | |
| 4,451,253 A | 5/1984 | Harman | |
| 4,559,054 A | 12/1985 | Bruck | |
| 4,576,591 A | 3/1986 | Kaye et al. | |

(Continued)

FOREIGN PATENT DOCUMENTS

| | | |
|---|---|---|
| EP | 1 216 721 | 6/2002 |
| EP | 1 518 549 | 2/2007 |

(Continued)

OTHER PUBLICATIONS

European Search Report for the counterpart application dated Mar. 12, 2018, 8 pages.

*Primary Examiner* — Kami A Bosworth
*Assistant Examiner* — Alexandra Lalonde
(74) *Attorney, Agent, or Firm* — Knobbe Martens Olson & Bear, LLP

(57) ABSTRACT

A drug pellet delivery system includes a housing having a cavity. A cartridge is positioned within the cavity and includes a body having a channel. The body includes a first pair of rails and a second pair of rails. A plunger is slidably disposed in the housing and the cartridge. The plunger is configured to move a drug depot through the channel and out of the housing. Kits and methods of use are disclosed.

20 Claims, 8 Drawing Sheets

(56) References Cited

U.S. PATENT DOCUMENTS

| | | |
|---|---|---|
| 4,624,848 A | 11/1986 | Lee |
| 4,774,091 A | 9/1988 | Yamahira et al. |
| 4,781,695 A | 11/1988 | Dalton |
| 4,892,538 A | 1/1990 | Patrick et al. |
| 4,909,250 A | 3/1990 | Smith |
| 5,024,655 A | 6/1991 | Freeman et al. |
| 5,024,841 A | 6/1991 | Chu et al. |
| 5,180,716 A | 1/1993 | Yaksh et al. |
| 5,207,678 A | 5/1993 | Harms et al. |
| 5,212,162 A | 5/1993 | Missel et al. |
| 5,330,768 A | 7/1994 | Park et al. |
| 5,487,739 A | 1/1996 | Aebischer et al. |
| 5,622,940 A | 4/1997 | Ostroff et al. |
| 5,694,920 A | 12/1997 | Abrams et al. |
| 5,752,930 A | 5/1998 | Rise et al. |
| 5,756,127 A | 5/1998 | Grisoni et al. |
| 5,834,001 A | 11/1998 | Dionne et al. |
| 5,928,130 A | 7/1999 | Schmidt |
| 5,980,927 A | 11/1999 | Nelson et al. |
| 6,001,386 A | 12/1999 | Ashton et al. |
| 6,007,843 A | 12/1999 | Drizen et al. |
| 6,015,557 A | 1/2000 | Tobinick et al. |
| 6,036,978 A | 3/2000 | Gombotz et al. |
| 6,083,534 A | 7/2000 | Wallach et al. |
| 6,086,614 A | 7/2000 | Mumme |
| 6,132,420 A | 10/2000 | Dionne et al. |
| 6,193,692 B1 | 2/2001 | Harris et al. |
| 6,203,813 B1 | 3/2001 | Gooberman |
| 6,214,370 B1 | 4/2001 | Nelson et al. |
| 6,235,289 B1 | 5/2001 | Aoki et al. |
| 6,242,004 B1 | 6/2001 | Rault |
| 6,277,969 B1 | 8/2001 | Le et al. |
| 6,450,937 B1 | 9/2002 | Mercereau et al. |
| 6,471,688 B1 | 10/2002 | Harper et al. |
| 6,478,776 B1 | 11/2002 | Rosenman et al. |
| 6,530,934 B1 | 3/2003 | Jacobsen et al. |
| 6,531,154 B1 | 3/2003 | Mathiowitz et al. |
| 6,551,290 B1 | 4/2003 | Elsberry et al. |
| 6,565,541 B2 | 5/2003 | Sharp |
| 6,571,125 B2 | 5/2003 | Thompson |
| 6,594,880 B2 | 7/2003 | Elsberry |
| 6,735,475 B1 | 5/2004 | Whitehurst et al. |
| 6,936,270 B2 | 8/2005 | Watson et al. |
| 6,971,998 B2 | 12/2005 | Rosenman et al. |
| 6,982,089 B2 | 1/2006 | Tobinick |
| 7,001,892 B1 | 2/2006 | Chmielewski et al. |
| 7,012,106 B2 | 3/2006 | Yuan et al. |
| 7,081,123 B2 | 7/2006 | Merboth et al. |
| 7,108,153 B2 | 9/2006 | Wood |
| 7,223,289 B2 | 5/2007 | Trieu et al. |
| 7,252,651 B2 | 8/2007 | Haider et al. |
| 7,252,685 B2 | 8/2007 | Bindseil et al. |
| 7,276,477 B2 | 10/2007 | Osslund et al. |
| 7,317,091 B2 | 1/2008 | Lazar et al. |
| 7,344,716 B2 | 3/2008 | Di Mauro et al. |
| 7,355,008 B2 | 4/2008 | Stavenhagen et al. |
| 7,700,100 B2 | 4/2010 | Johnson et al. |
| 7,727,954 B2 | 6/2010 | McKay |
| 7,741,273 B2 | 6/2010 | McKay |
| 7,955,301 B1 | 6/2011 | McKay |
| 8,029,478 B2 | 10/2011 | Zanella |
| 8,084,582 B2 | 12/2011 | Dahiyat et al. |
| 8,221,358 B2 | 7/2012 | McKay |
| 8,246,571 B2 | 8/2012 | Simonton et al. |
| 8,267,895 B2 | 9/2012 | McKay |
| 8,357,388 B2 | 1/2013 | McKay |
| 8,481,064 B2 | 7/2013 | McKay |
| 8,702,677 B2 | 4/2014 | Simonton et al. |
| 8,715,223 B2 | 5/2014 | McKay |
| 8,998,854 B2 | 4/2015 | McKay |
| 9,764,122 B2 | 9/2017 | Clay et al. |
| 9,775,978 B2 | 10/2017 | Clay et al. |
| D802,755 S | 11/2017 | Snyder |
| D802,756 S | 11/2017 | Snyder |
| D802,757 S | 11/2017 | Snyder et al. |
| D809,652 S | 2/2018 | Snyder et al. |
| 2001/0020147 A1 | 9/2001 | Staniforth et al. |
| 2001/0031940 A1* | 10/2001 | Loos ............... A61M 37/0069 604/15 |
| 2001/0043915 A1 | 11/2001 | Frey |
| 2002/0082583 A1 | 6/2002 | Lerner |
| 2002/0198527 A1 | 12/2002 | Muckter |
| 2003/0004491 A1 | 1/2003 | Tenhuisen et al. |
| 2003/0036673 A1 | 2/2003 | Schmidt |
| 2003/0171637 A1 | 9/2003 | Terwilliger et al. |
| 2003/0023310 A1 | 12/2003 | Lubock et al. |
| 2004/0015133 A1 | 1/2004 | Karim |
| 2004/0064088 A1 | 4/2004 | Gorman et al. |
| 2004/0064193 A1 | 4/2004 | Evans et al. |
| 2004/0065615 A1 | 4/2004 | Hooper et al. |
| 2004/0082908 A1 | 4/2004 | Whitehurst et al. |
| 2004/0098113 A1 | 5/2004 | Forsell et al. |
| 2004/0106914 A1 | 6/2004 | Coppeta et al. |
| 2004/0111118 A1 | 6/2004 | Hill et al. |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2005/0070843 A1 | 3/2005 | Gonzales |
| 2005/0074481 A1 | 4/2005 | Brekke et al. |
| 2005/0137579 A1 | 6/2005 | Heruth et al. |
| 2005/0152905 A1 | 7/2005 | Omoigui |
| 2005/0152949 A1 | 7/2005 | Hotchkiss et al. |
| 2005/0177118 A1 | 8/2005 | Hoganson et al. |
| 2005/0178779 A1 | 8/2005 | Wood |
| 2005/0245906 A1 | 11/2005 | Makower et al. |
| 2005/0249775 A1 | 11/2005 | Falotico et al. |
| 2006/0046960 A1 | 3/2006 | McKay et al. |
| 2006/0046961 A1 | 3/2006 | McKay et al. |
| 2006/0084943 A1 | 4/2006 | Roseman et al. |
| 2006/0100622 A1 | 5/2006 | Jackson |
| 2006/0121032 A1 | 6/2006 | Dahiyat et al. |
| 2006/0253100 A1 | 11/2006 | Burright et al. |
| 2006/0264839 A1 | 11/2006 | Veasey et al. |
| 2007/0043359 A1 | 2/2007 | Altarac et al. |
| 2007/0055378 A1 | 3/2007 | Ankney et al. |
| 2007/0123863 A1 | 5/2007 | Winslow et al. |
| 2007/0219564 A1 | 9/2007 | Rue et al. |
| 2008/0228193 A1 | 9/2008 | Matityahu |
| 2009/0053211 A9 | 2/2009 | Lazar et al. |
| 2009/0088809 A1 | 4/2009 | Fisher et al. |
| 2009/0182267 A1 | 7/2009 | Painchaud et al. |
| 2010/0106132 A1 | 4/2010 | Simonton |
| 2010/0106136 A1 | 4/2010 | Simonton |
| 2010/0106137 A1 | 4/2010 | Simonton et al. |
| 2011/0106110 A1 | 5/2011 | McKay |
| 2011/0313393 A1 | 12/2011 | Zanella |
| 2012/0053561 A1* | 3/2012 | Simonton ......... A61M 37/0069 604/506 |
| 2012/0142648 A1 | 6/2012 | Biggs et al. |
| 2012/0142747 A1 | 6/2012 | Wilsey et al. |
| 2016/0022973 A1 | 1/2016 | Clay et al. |
| 2017/0354811 A1 | 12/2017 | Clay et al. |
| 2017/0368323 A1 | 12/2017 | Snyder |
| 2018/0001072 A1 | 1/2018 | Clay et al. |

FOREIGN PATENT DOCUMENTS

| | | |
|---|---|---|
| FR | 1 270 590 | 9/1961 |
| FR | 2 007 684 | 1/1970 |
| FR | 2 231 355 | 12/1974 |
| GB | 1379358 | 1/1975 |
| WO | WO 93/20859 | 10/1993 |
| WO | WO 94/01166 | 1/1994 |
| WO | WO 99/052573 | 10/1999 |
| WO | WO 2001/062272 | 8/2001 |
| WO | WO 2002/034116 | 5/2002 |
| WO | WO 2004/009776 | 1/2004 |
| WO | WO 2004/050688 | 6/2004 |
| WO | WO 2004/084819 | 10/2004 |
| WO | 2016014300 A1 | 1/2016 |

* cited by examiner

DRUG PELLET DELIVERY SYSTEM AND METHOD

TECHNICAL FIELD

The present disclosure generally relates to drug delivery devices, and more particularly to a drug pellet delivery system that includes features that prevent drug pellets from being misdirected as they move through a drug delivery device.

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug pellets, such as, for example, drug depots have been developed, which allow a drug to be introduced or administered to sites beneath the skin of a patient. The drug depot releases the drug over a period of time. Drug depots allow the drug to be released from the depot in a relatively uniform dose over weeks, months or even years. Administering drugs using drug depots is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug delivery devices have been developed to implant drug depots within a patient. These devices have a cartridge that contains one or more drug depots. A rod is moved within the cartridge to push the drug depot out of the cartridge. However, the drug depots can be misdirected as they are pushed through the cartridge by the rod. In some cases, the drug depots have the potential to lift and escape a pathway of the cartridge, thus preventing the drug depots from being properly expelled from the cartridge or, in some cases, from being expelled at all. This disclosure describes improvements over these prior art technologies.

SUMMARY

In one embodiment, a drug pellet delivery system system is provided. The drug pellet delivery system includes a housing having a cavity. A cartridge is positioned within the cavity and includes a body having a channel. One or a plurality of drug pellets, such as, for example, drug depots may be positioned within the channel. The body includes a first pair of rails and a second pair of rails on opposite sides of the channel. A plunger is slidably disposed through the housing and the channel. The plunger includes a push rod to move the drug depots through the channel and out of the housing. The rails are configured to prevent the drug depots from being misdirected as the drug depots move through the channel. In some embodiments, kits and methods of use are disclosed.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
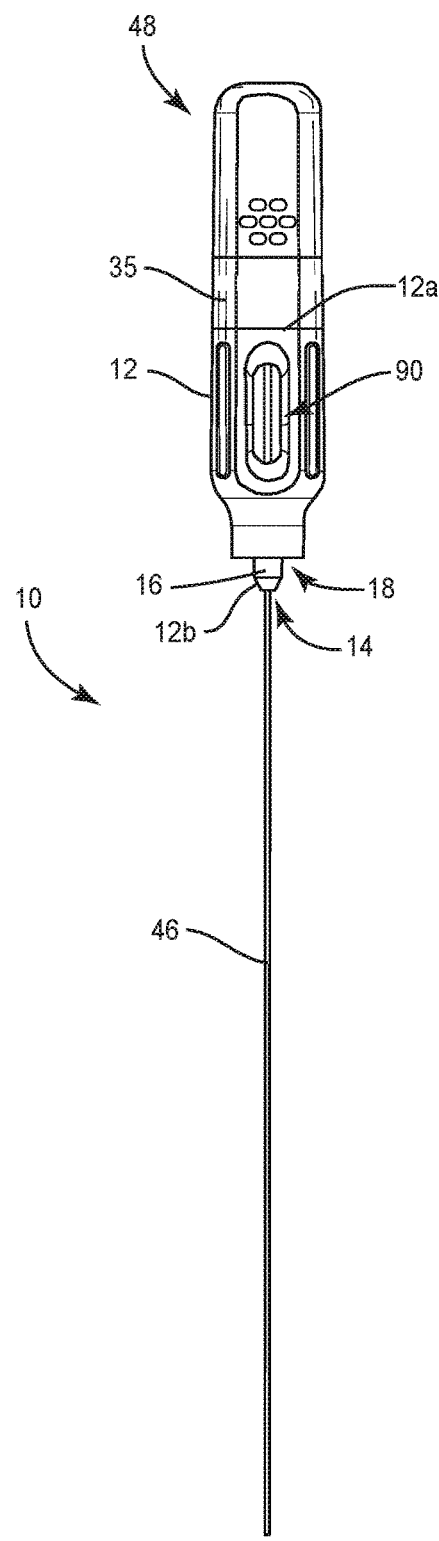
FIG. 1 is a front view of one embodiment of components of a drug pellet delivery system in accordance with the present principles of the present disclosure.

The exemplary embodiments of a drug pellet delivery system and related methods are discussed in terms of medical devices for delivering drug pellets, such as, for example, one or a plurality of drug depots. In some embodiments, the system and method may be employed in applications that require at least one drug depot to be implanted within a patient's body.

In some embodiments, the drug pellet delivery system includes a cartridge having directional rails that block and redirect a delivery plunger and drug depots or pellets to maintain alignment through a pellet pathway of the cartridge. In some embodiments, the cartridge includes upper and lower directional rails. In some embodiments, the upper directional rails maintain the directional alignment of the delivery plunger and the lower directional rails maintain the directional alignment of the drug depots or pellets during deployment. It has been found that the directional rails substantially improve the function of the drug pellet delivery system facilitating better deployment of the drug depots or pellets and preventing jamming of the delivery plunger and/or the drug depots or pellets.

In some embodiments, one or all of the components of the drug pellet delivery system may be disposable, peel-pack, pre-packed sterile devices. In some embodiments, the components of the drug pellet delivery system are configured for one time use and are disposed after they are used one time. However, it is contemplated that one or all of the components of the drug pellet delivery system may be reusable. The drug pellet delivery system may be configured as a kit with multiple sized and configured components, including, for example, various drug pellets or depots. In some embodiments, the drug pellets or depots are pre-loaded into a delivery device. In some embodiments, one or more of the components of the drug pellet delivery system are configured to be sterilized.

In some embodiments, the disclosed drug pellet delivery system and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drug pellets or drug depots to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a drug pellet delivery system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-13, there are illustrated components of a drug pellet delivery system 10 in accordance with the principles of the present disclosure.

The components of drug pellet delivery system 10 can be fabricated from biologically acceptable materials suitable for medical applications, including metals, synthetic polymers, ceramics and bone material and/or their composites, depending on the particular application and/or preference of a medical practitioner. For example, the components of drug pellet delivery system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of drug pellet delivery system 10 may have material composites, including the above materials, to achieve various desired characteristics such as strength, rigidity, elasticity, compliance, biomechanical performance, durability and radiolucency or imaging preference. The components of drug pellet delivery system 10, individually or collectively, may also be fabricated from a heterogeneous material such as a combination of two or more of the above-described materials. The components of drug pellet delivery system 10 may be monolithically formed, integrally connected or include fastening elements and/or instruments, as described herein.

In some embodiments, drug pellet delivery system 10 is used to deliver one or a plurality of drug pellets or drug depots. In some embodiments, the drug pellet or drug depots may include an active agent, such as, for example, one or a plurality of drugs.

Drug pellet delivery system 10 includes a housing 12 having an inner surface that defines a cavity 14. Housing 12 includes openings that extend through opposite proximal and distal end surfaces 12a, 12b of housing 12. The openings are in communication with cavity 14. In some embodiments, a distal end of housing 12 includes a nozzle 16 and an aperture 18 defined by an inner surface of housing 12 and an outer surface of nozzle 16. Aperture 18 is spaced apart from cavity 14 by a wall such that aperture 18 is not in communication with cavity 14. The inner surface of housing 12 that defines a portion of aperture 18 is threaded such that a hollow tube, such as, for example, cannula 20 shown in FIG. 2 can be positioned over nozzle 16 such that threads of cannula 20 engage the threaded inner surface of housing 12 that defines a portion of aperture 18 to couple cannula 20 to housing 12. In some embodiments, nozzle 16 is positioned within cannula 20 and cannula 20 is rotated relative to housing 12 to mate threads of cannula 20 with the threaded inner surface of housing 12 that defines a portion of aperture 18 to couple cannula 20 to housing 12. In some embodiments, cannula 20 can be variously connected with housing 12, such as, for example, monolithic, integral connection, frictional engagement, threaded engagement, mutual grooves, screws, adhesive, nails, barbs and/or raised elements. Nozzle 16 includes a conduit 25 that is in communication with cavity 14 and extends entirely through nozzle 16. Conduit 25 is coaxial with cavity 14. In some embodiments, conduit 25 has a circular cross sectional configuration. In some embodiments, conduit 25 may have various cross section configurations, such as, for example, oval, oblong, triangular, rectangular, square, polygonal, irregular, uniform, non-uniform, variable, tubular and/or tapered.

Figure 4:
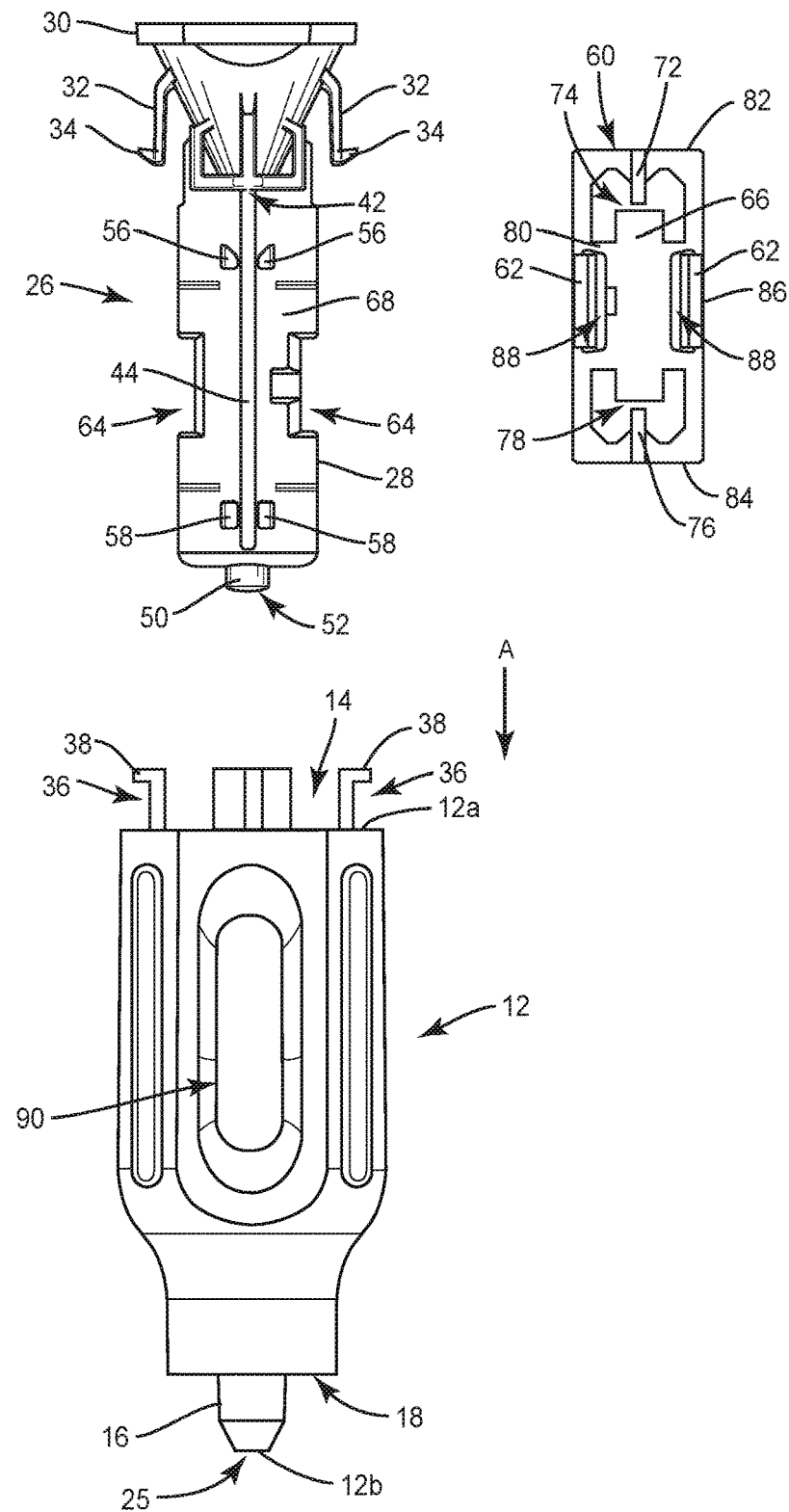
FIG. 4 is a front view of components of the drug pellet delivery system shown in FIG. 1, with parts separated.
Figure 5:
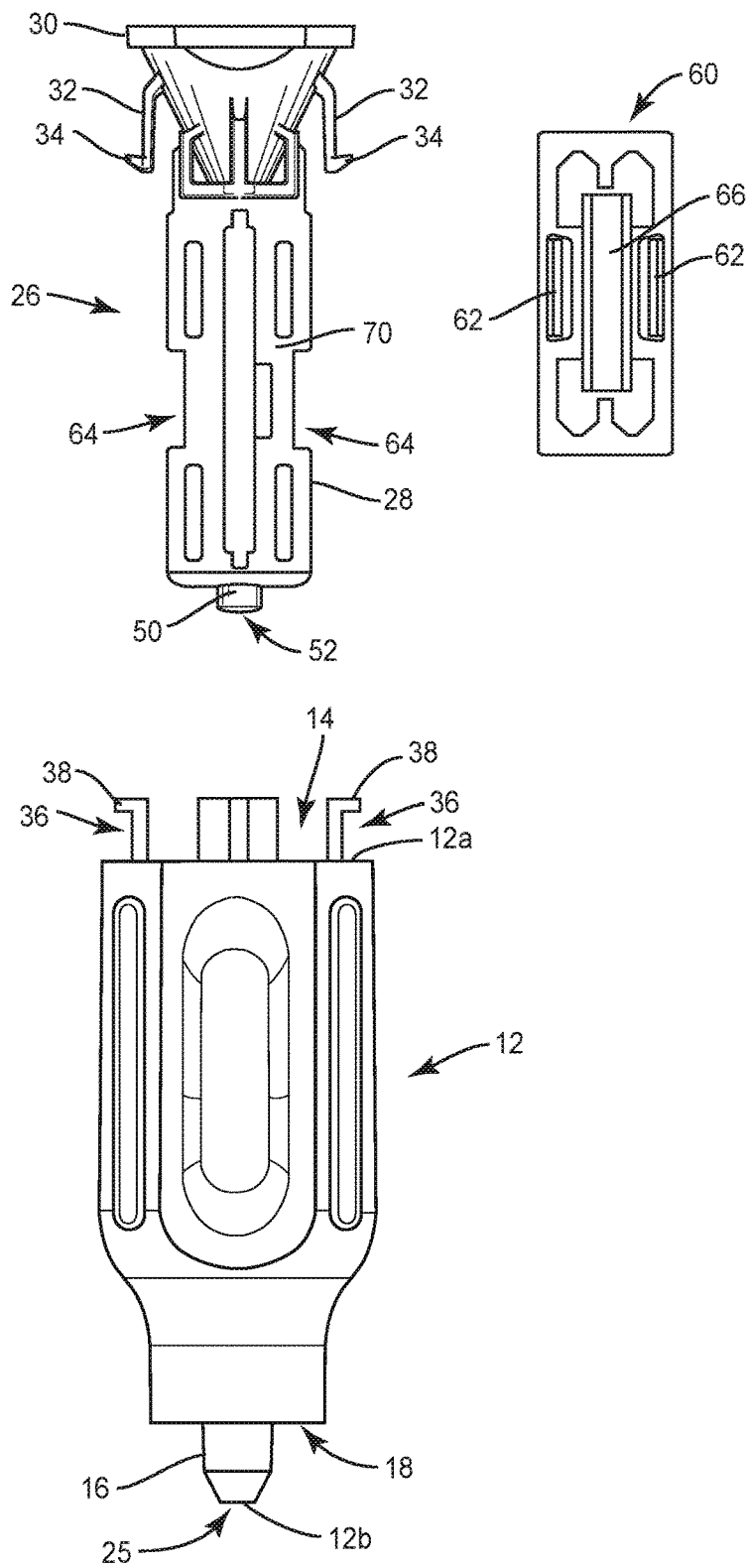
FIG. 5 is a back view of components of the drug pellet delivery system shown in FIG. 1, with parts separated.
Figure 7:
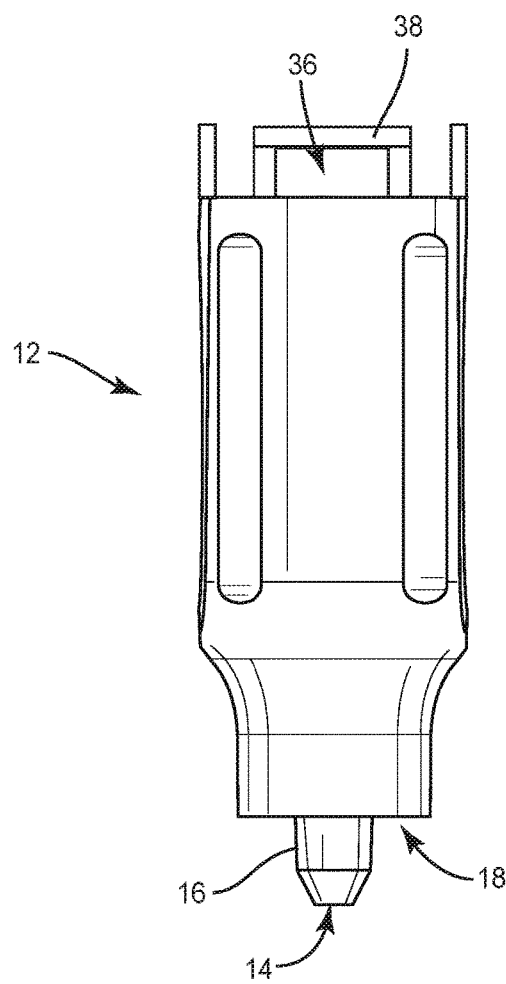
FIG. 7 is a left side view of a component of the drug pellet delivery system shown in FIG. 1.
Figure 8:
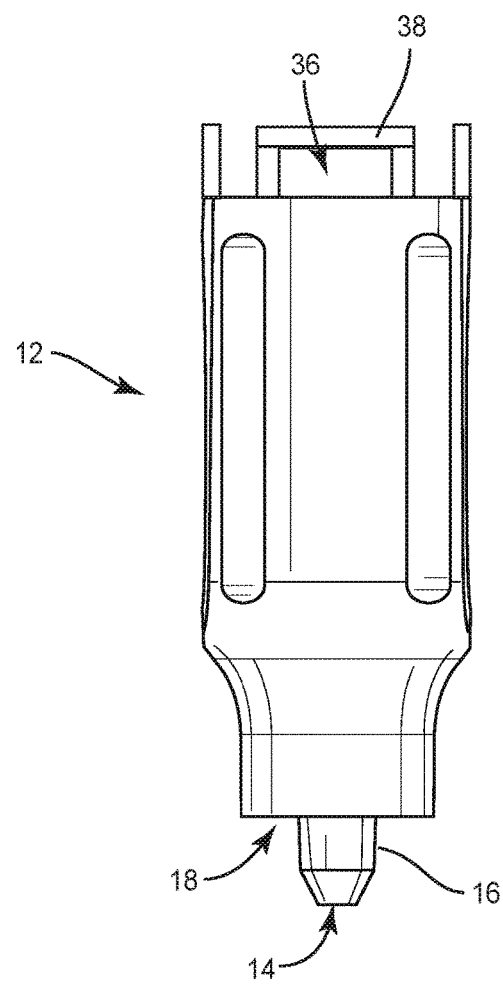
FIG. 8 is a right side view of a component of the drug pellet delivery system shown in FIG. 1.

A cartridge 26 is positioned within cavity 14. Cartridge 26 comprises a body 28 and a funnel portion 30 coupled to a proximal end of body 28, as shown in FIGS. 4 and 5. In some embodiments, funnel portion 30 is integrally formed with body 28. That is, cartridge 26 is monolithic such that funnel portion 30 is permanently fixed to body 28 and cannot be removed from body 28 without breaking funnel portion 30 and/or body 28. In some embodiments, funnel portion 30 comprises a pair of tabs, such as, for example, extensions 32 that each include a barb 34. Barbs 34 are configured to be positioned within openings 36 in tabs, such as, for example, projections 38 of housing 12 to couple cartridge 26 to housing 12 such that cartridge 26 is fixed relative to housing 12. Openings 36 and projections 38 are shown in FIGS. 7 and 8, for example. In some embodiments, extensions 32 are resilient such that extensions 32 can deflect toward and away from funnel portion 30. Barbs 34 are tapered such that cartridge 26 can be inserted into cavity 14 by positioning cartridge 26 above housing 12 and moving cartridge 26 relative to housing 12 in the direction shown by arrow A in FIG. 4. As cartridge 26 moves relative to housing 12 in the direction shown by arrow A in FIG. 4, barbs 34 engage projections 38, which forces extensions 32 inwardly toward funnel portion 30. Cartridge 26 is moved further relative to housing 12 in the direction shown by arrow A in FIG. 4 until barbs 34 are aligned with openings 36, which causes extensions 32 to move outwardly and away from funnel portion 30 to position barbs 34 within openings 36 and fix cartridge 26 relative to housing 12. In some embodiments, extensions 32 are biased outwardly, away from funnel portion 30. This prevents barbs 34 from being removed from openings 36. That is, to remove barbs 34 from openings 36, a force must be applied to extensions 32 to force extensions 32 toward one another. When the housing 12 is assembled, extensions 32 are surrounded by a ring 35. Ring 35 also surrounds the funnel portion 30 and sits atop the housing 12 and abuts the proximal portion of the plunger 48. Ring 35 protects the extensions 32 from accidental uncoupling.

Figure 6:
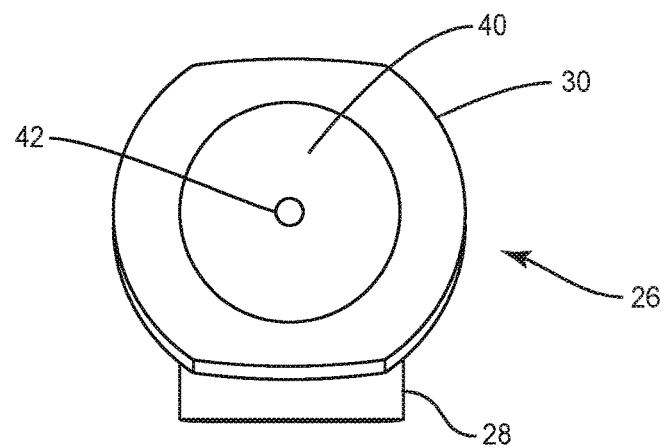
FIG. 6 is an end, perspective view of a component of the drug pellet delivery system shown in FIG. 1.

Funnel portion 30 comprises a lip that sits atop the ring 35, as shown in FIG. 1, and conical inner surface that defines a tapered cavity 40, as shown in FIG. 6. Funnel portion 30 comprises an opening 42 in the conical inner surface that is in communication with cavity 40. Body 28 comprises a channel 44 that is aligned with opening 42 such that a rod, such as, for example, a push rod 46 of a plunger 48 can be inserted through cavity 40 and opening 42 and enter channel 44. In some embodiments, channel 44 is defined by a concave inner surface of body 28. In some embodiments, channel 44 has a semi-circular cross sectional configuration. In some embodiments, channel 44 is coaxial with cavity 14, conduit 25, cavity 40 and/or opening 42. Body 28 comprises a tip, such as, for example, a nipple portion 50, as shown in FIGS. 4, 5, 9 and 12. An opening or passageway, such as, for example, a lumen 52 extends through nipple portion 50 and is aligned with channel 44 such that push rod 46 can extend through cavity 14, cavity 40, opening 42, channel 44, lumen 52 and conduit 25 simultaneously. Channel 44 is configured to have one or a plurality of drug depots, such as, for example, drug pellets 54 shown in FIGS. 9 and 12 positioned therein. Push rod 46 and drug pellets 54 each have a maximum diameter that is less than or equal to a maximum diameter of conduit 25, opening 42 and lumen 52. The maximum diameter of push rod 46 is equal to or greater than a maximum diameter of drug pellets 54 such that push rod 46 can be inserted through cavity 40 and opening 42. Push rod 46 is moved relative to housing 12 and cartridge 26 in the direction shown by arrow A in FIG. 4 such that a distal end of push rod 46 moves into channel 44. Moving push rod 46 further in the direction shown by arrow A in FIG. 4 causes the distal end of push rod 46 to engage a drug pellet 54 within channel 44 and move the drug pellet 54 out of channel 44 through lumen 52, as discussed herein and shown in FIG. 12. After the drug pellet 54 exits lumen 52, the drug pellet 54 can move through conduit 25 and into passageway 24 of cannula 20 to deliver the drug pellet to a location within a patient, as discussed herein. In some embodiments, drug pellets 54 have a maximum diameter that is equal to or less than a depth of channel 44 such that drug pellets 54 are disposed entirely within channel 44 when drug pellets 54 are positioned within channel 44. In some embodiments, drug pellets 54 have a maximum diameter that is greater than the depth of channel 44 such that a portion of drug pellets 54 extend out of channel 44 when drug pellets 54 are positioned within channel 44. Opening 42 is coaxial with lumen 52 and conduit 25, as discussed herein. In some embodiments, opening 42 and/or lumen 52 have a circular cross sectional configuration. In some embodiments, opening 42 and/or lumen 52 may have various cross section configurations, such as, for example, oval, oblong, triangular, rectangular, square, polygonal, irregular, uniform, non-uniform, variable, tubular and/or tapered.

Figure 9:
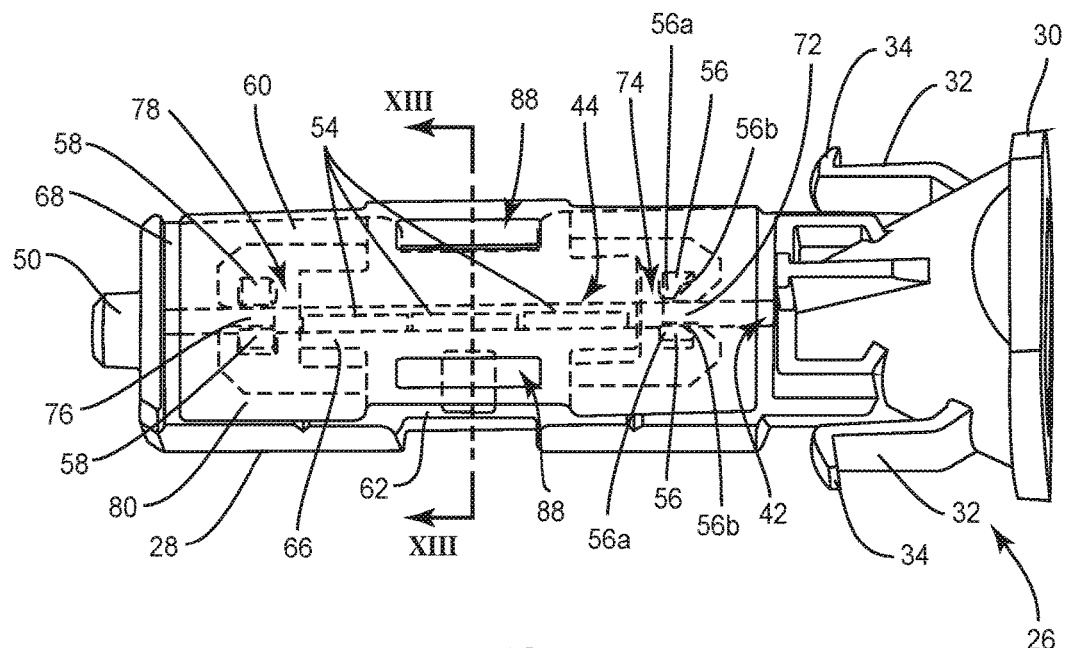
FIG. 9 is a perspective, front view of some of the components of the drug pellet delivery system shown in FIG. 1.
Figure 10:
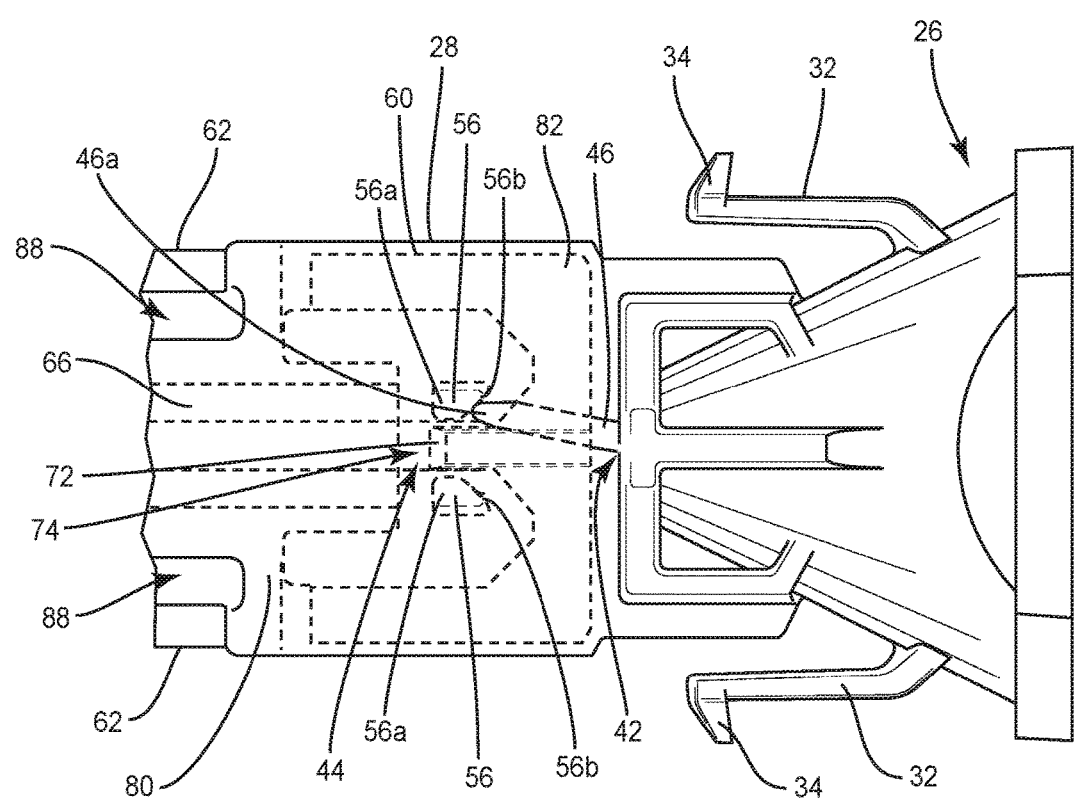
FIG. 10 is a close up, front view of some of the components of the drug pellet delivery system shown in FIG. 1.
Figure 11:
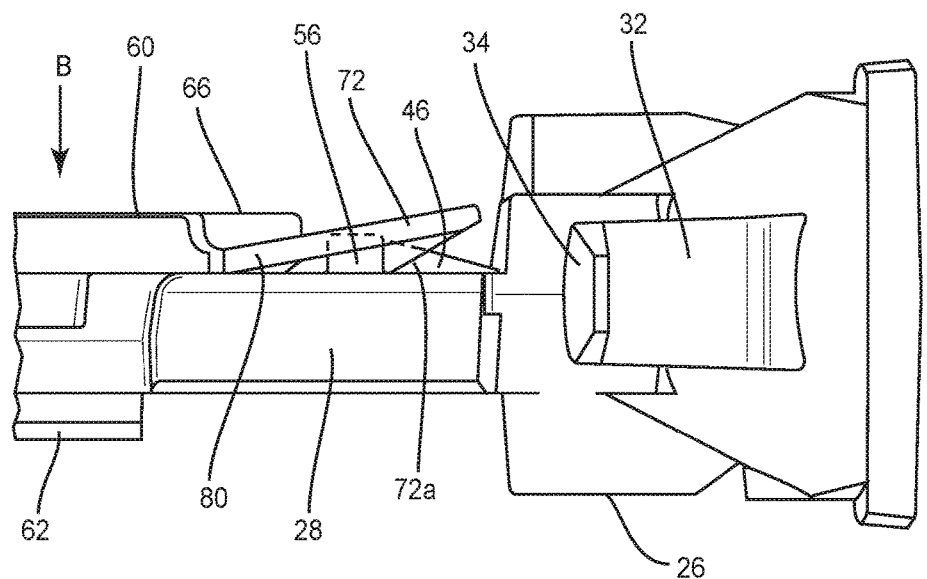
FIG. 11 is a close up, side view of some of the components of the drug pellet delivery system shown in FIG. 1.

In some embodiments, body 28 includes a first pair of directional rails 56, as shown in FIGS. 4, 9, 10 and 12. Rails 56 are positioned adjacent to opening 42 and are spaced apart from one another by channel 44. Rails 56 extend outwardly from an outer surface of body 28 and each include a first portion 56a that extends parallel to a longitudinal axis defined by channel 44 and a second tapered portion 56b. Portions 56b extend transverse to the longitudinal axis defined by channel 44. Portions 56b are each tapered from a proximal end of body 28 to an interface between portions 56a, 56b such that a distance between portions 56b is greater at the proximal end of body 28 than at the interface between portions 56a, 56b. In some embodiments, rails 56 each extend parallel to the longitudinal axis defined by channel 44 along the entire length of rails 56. Rails 56 are configured to block and redirect push rod 46 of plunger 48 to maintain alignment of push rod 46 through channel 44, as shown in FIGS. 10 and 11. That is, rails 56 prevent push rod 46 from falling out of channel 44 as push rod 46 moves within channel 44 in direction A shown FIG. 4. For example, if push rod 46 is inserted through opening 42 and into channel 44 such that push rod 46 extends transverse to the longitudinal axis defined by channel 44, a distal tip 46a of push rod 46 will engage an inner surface of one of portions 56b, as shown in FIG. 10. As push rod 46 moves within channel 44 in direction A shown FIG. 4, portions 56b will redirect push rod 46 between portions 56a such that push rod 46 is oriented parallel to the longitudinal axis defined by channel 44. In some embodiments, tip 46a of push rod 46 is blunt so as to prevent damage to drug pellets 54.

Figure 12:
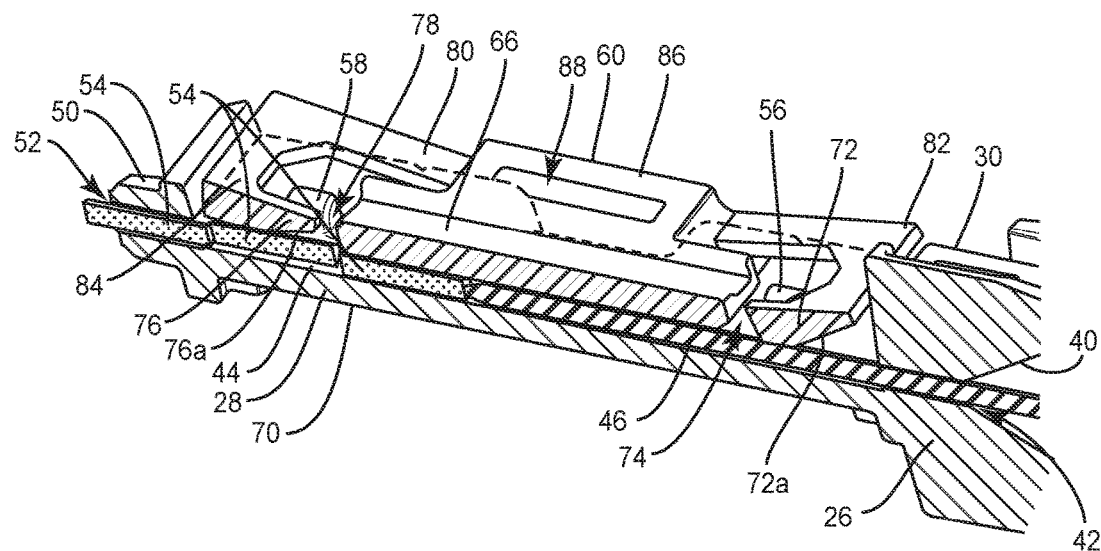
FIG. 12 is a perspective, side, cross section view of some of the components of the drug pellet delivery system shown in FIG. 1.
Figure 13:
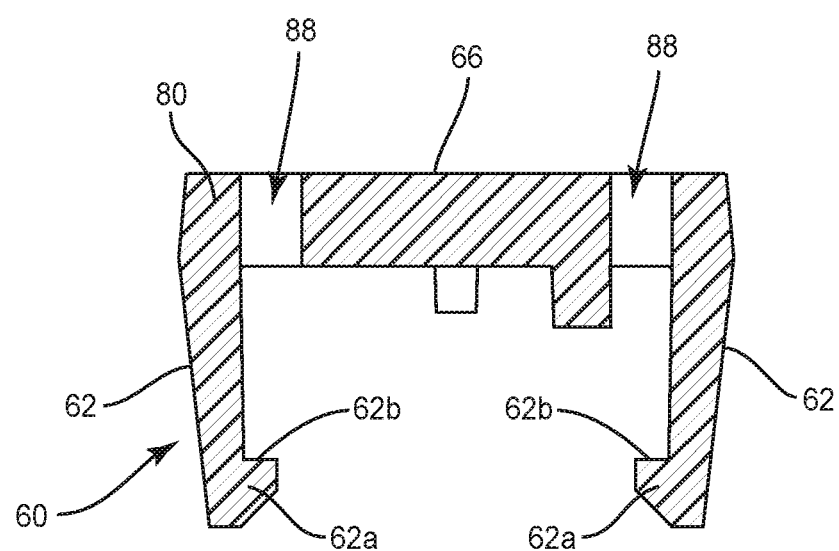
FIG. 13 is an end, cross section view of a component of the drug pellet delivery system shown in FIG. 1 taken along lines XIII-XIII in FIG. 9.

In some embodiments, body 28 includes a second pair of directional rails 58, as shown in FIGS. 4, 9 and 12. Rails 58 are positioned adjacent to nipple portion 50 and are spaced apart from one another by channel 44. Rails 58 each extend outwardly from the outer surface of body 28 and each extend parallel to the longitudinal axis defined by channel 44 along the entire length of rails 58. Rails 58 are configured to block and redirect drug pellets 54 to maintain alignment of drug pellets 54 through channel 44, as shown in FIG. 12. That is, rails 58 prevent drug pellets 54 from falling out of channel 44 (e.g., move laterally) as drug pellets 54 move within channel 44 in direction A shown FIG. 4. For example, if drug pellets 54 begin to move laterally within channel 44, drug pellets 54 will engage inner surfaces of rails 58 to redirect drug pellets 54 between rails 58 such that drug pellets 54 are positioned within channel 44. This maintains alignment of drug pellets 54 with channel 44 such that drug pellets 54 are aligned with lumen 52 such that push rod 46 can push drug pellets 54 through channel 44 and out of cartridge 26 through lumen 52. In some embodiments, rails 58 are shaped and configured similar to rails 56 described herein. That is, rails 58 may each include a portion that is parallel to the longitudinal axis defined by channel 44 and a tapered portion that extends transverse to the longitudinal axis defined by channel 44.

In some embodiments, a cover 60 is removably coupled to cartridge 26 to assist in maintaining drug pellets 54 within channel 44. Cover 60 comprises a pair of tabs 62 that are positioned within grooves 64 in body 28 to attach cover 60 to cartridge 26. Tabs 62 extend outwardly from a frame 80 of cover 60. A wall 66 of cover 60 is configured to be positioned over channel 44 such that wall 66 covers at least a portion of channel 44 to maintain drug pellets 54 within channel 44. Wall 66 engages a front surface 68 of body 28. Front surface 68 is shown in FIG. 4, for example. Channel 44 extends into front surface 68 and rails 56, 58 each extend outwardly from front surface 68. In some embodiments, tabs 62 are resilient such that tabs 62 can deflect toward and away from wall 66 and/or frame 80. In some embodiments, tabs 62 each include a tapered barb 62a having a surface 62b that engages a back surface 70 (FIG. 5) of body 28 when wall 66 engages front surface 68. Back surface 70 is opposite front surface 68. A distance between wall 66 and surface 62b is slightly greater than a distance between front surface 68 and back surface 70 such that cover 60 can be coupled to body 28 by positioning cover 60 above cartridge 26 with tabs 62 aligned with grooves 64. Cover 60 is moved relative to body 28 in the direction shown by arrow B in FIG. 11. As cover 60 moves relative to body 28 in the direction shown by arrow B in FIG. 11, barbs 62a engage front surface 68, which forces tabs 62 outwardly such that a distance between barbs 62a increases. Cover 60 is moved further relative to body 28 in the direction shown by arrow B in FIG. 11 such that barbs 62a move along a side surface of body 28 that extends between front and back surfaces 68, 70. As barbs 62a move passed the side surface of body 28, tabs 62 move inwardly to decrease the distance between barbs 62a such that surfaces 62b engage back surface 70 to fix cover 60 relative to body 28. In some embodiments, tabs 62 are biased inwardly, toward one another such that tabs 62 snap into place about cartridge 26 as cover 60 is moved relative to cartridge 26 in the direction shown by arrow B in FIG. 11 as described above.

In some embodiments, cover 60 includes a projection 72 having a tip that is spaced apart from wall 66 by a gap 74 and a projection 76 having a tip that is spaced apart from wall 66 by a gap 78, as shown in FIGS. 4, 9 and 12. Projections 72, 76 are connected to wall 66 by frame 80, as best shown in FIG. 9. Tabs 62 extend outwardly from frame 80. In some embodiments, gaps 74, 78 allow opposite proximal and distal ends 82, 84 of frame 80 to deflect relative to a middle portion 86 of frame 80, as shown in FIG. 12, for example. Tabs 62 extend from middle portion 86.

Cover 60 is positioned relative to cartridge 26 such that when wall 66 of cover 60 engages front surface 68 of body 28, projection 72 is positioned between rails 56 and projection 76 is positioned between rails 58. In some embodiments, projection 72 includes a ramp 72a that is tapered from the tip of projection 72 to proximal end 82 of frame 80 and projection 76 includes a ramp 76a that is tapered from distal end 84 of frame 80 to the tip of projection 76, as best shown in FIG. 12.

Ramp 72a is configured to redirect tip 46a of push rod 46 into channel 44 should push rod 46 be inserted through opening 42 and into channel 44 in a direction that is transverse to the longitudinal axis defined by channel 44, as shown in FIG. 11, for example. That is, if push rod 46 is inserted into channel 44 in a direction that is transverse to the longitudinal axis defined by channel 44, push rod will engage ramp 72a such that proximal end 82 of frame 80 deflects upwardly relative to middle portion 86 of frame 80 such that proximal end 82 extends transverse to middle portion 86. Tip 46a will slide along ramp 72a to guide push rod 46 into channel 44 such that push rod 46 is coaxial with channel 44. In some embodiments, proximal end 82 extends transverse to middle portion 86 when push rod 46 is positioned within channel 44, as shown in FIG. 12. In some embodiments, once push rod 46 is coaxial with channel 44, proximal end 82 will move relative to middle portion 86 such that proximal end 82 extends parallel to middle portion 86. As such, rails 56 prevent push rod 46 from moving laterally within channel 44 and projection 72 prevents push rod 46 from moving upwardly out of channel 44 to orient push rod 46 such that push rod 46 is coaxial with channel 44 as push rod 46 moves through channel 44.

Ramp 76a is configured to redirect drug pellets 54 into channel 44 should drug pellets 54 begin to lift out of channel 44. That is, if drug pellets 54 move within channel 44 such that drug pellets 54 are transverse to the longitudinal axis defined by channel 44, drug pellets 54 will engage ramp 76a such that distal end 84 of frame 80 deflects upwardly relative to middle portion 86 of frame 80 such that distal end 84 extends transverse to middle portion 86, as shown in FIG. 12. Drug pellets 54 will slide along ramp 76a to guide drug pellets 54 into channel 44 such that drug pellets 54 are coaxial with channel 44. In some embodiments, distal end 84 extends transverse to middle portion 86 when drug pellets 54 are positioned within channel 44, as shown in FIG. 12. In some embodiments, once drug pellets 54 are coaxial with channel 44, distal end 84 will move relative to middle portion 86 such that distal end 84 extends parallel to middle portion 86. As such, rails 58 prevent drug pellets 54 from moving laterally within channel 44 and projection 76 prevents drug pellets 54 from moving upwardly out of channel 44 to orient drug pellets 54 such that drug pellets 54 are coaxial with channel 44 as drug pellets 54 move through channel 44.

In some embodiments, cover 60 includes apertures 88 between wall 66 and tabs 62, as shown in FIGS. 4, 9 and 10, for example. Apertures 88 are spaced apart from one another by wall 66. It is envisioned that apertures 88 allow tabs 62 to deflect inwardly and outwardly relative to wall 66 to increase and decrease the distance between barbs 62a to couple cover 60 to cartridge 26, as discussed herein. Apertures 88 have a substantially rectangular configuration. In some embodiments, apertures 88 may have various configurations, such as, for example, oval, oblong, triangular, rectangular, square, polygonal, irregular, uniform, non-uniform, variable, tubular and/or tapered.

In assembly, operation and use, system 10 is employed with a surgical procedure, such as, to deliver one or more drug pellets or drug depots, such as, for example drug pellets 54 to a target location within a patient.

For example, system 10 and accessories thereof, described above, can be employed to implant one or more drug pellets within a patient at a selected location, such as, for example, a surgical site. In use, a medical practitioner obtains access to the surgical site in any appropriate manner. It is envisioned that system 10 can be used in any existing surgical method or technique including open surgery, mini-open surgery, minimally invasive surgery and percutaneous surgical implantation. One or more drug pellets can be delivered to the target location using system 10.

System 10 may be assembled by inserting one or more drug pellets or drug depots, such as, for example, drug pellets 54 within channel 44. In some embodiments, the drug pellets each include the same drug or combination of drugs. In some embodiments, the drug pellets may include different drugs, different combinations of drugs and/or different amounts of drugs. Cover 60 is coupled to cartridge 26, as discussed herein. In particular, cover 60 is positioned above cartridge 26 with tabs 62 aligned with grooves 64. Cover 60 is moved relative to body 28 in the direction shown by arrow B in FIG. 11. As cover 60 moves relative to body 28 in the direction shown by arrow B in FIG. 11, barbs 62a engage front surface 68, which forces tabs 62 outwardly such that the distance between barbs 62a increases. Cover 60 is moved further relative to body 28 in the direction shown by arrow B in FIG. 11 such that barbs 62a move along the side surface of body 28 that extends between front and back surfaces 68, 70. As barbs 62a move passed the side surface of body 28, tabs 62 move inwardly to decrease the distance between barbs 62a such that surfaces 62b engage back surface 70 to fix cover 60 relative to body 28. This allows cover 60 snaps into place about cartridge 26.

Cartridge 26 and cover 60 are then positioned within cavity 14 of housing 12 to couple cartridge 26 to housing, as discussed herein. In particular, cartridge 26 is positioned above housing 12. Cartridge 26 is moved relative to housing 12 in the direction shown by arrow A in FIG. 4. As cartridge 26 moves relative to housing 12 in the direction shown by arrow A in FIG. 4, barbs 34 engage projections 38, which forces extensions 32 inwardly toward body 28. Ring 35 can be placed adjacent to housing such that barbs 36, projections 38, and extensions 32 are surrounded. Cartridge 26 is moved further relative to housing 12 in the direction shown by arrow A in FIG. 4 until barbs 34 are aligned with openings, which causes extensions 32 to move outwardly away from body 28 to position barbs 34 within openings 36 and fix cartridge 26 relative to housing 12. In some embodiments, cover 60 comprises a clear, transparent or translucent material and housing 12 comprises a window 90 such that push rod 46 and/or one or more of the drug pellets in channel 44 can be viewed through window 90. Window 90 also allows visual confirmation when tip 46a of push rod 46 engages a proximal one of the drug pellets within channel 44. In some embodiments, cannula 20 has a length sufficient to allow at least a portion of housing 12 that includes window 90 to be positioned above the skin while the distal end of cannula 20 is adjacent to the target location. This allows a medical practitioner to visualize movement of push rod 46 and/or drug pellets 54 in channel 44 through window 90.

Figure 1A:
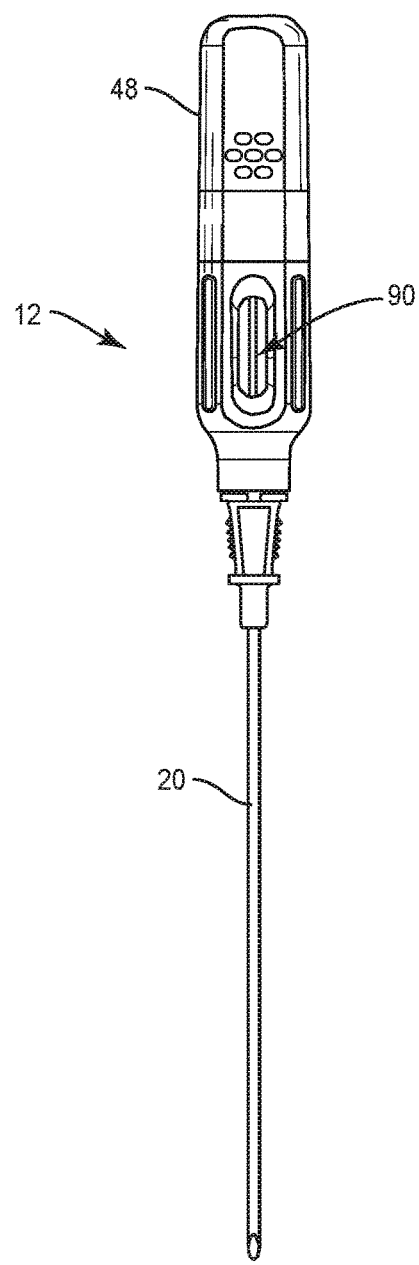
FIG. 1A is a front view, in part phantom, of components of the drug pellet delivery system shown in FIG. 1.

Cannula 20 is coupled to housing 12, as discussed herein, and shown in FIG. 1A. In particular, cannula 20 is positioned over nozzle 16 such that threads 22 of cannula 20 engage the threaded inner surface of housing 12 that defines a portion of aperture 18 to couple cannula 20 to housing 12. When cannula 20 is coupled to housing 12, passageway 24 is coaxial with cavity 14, cavity 40, opening 42, channel 44, lumen 52 and conduit 25.

Figures 2, 3:
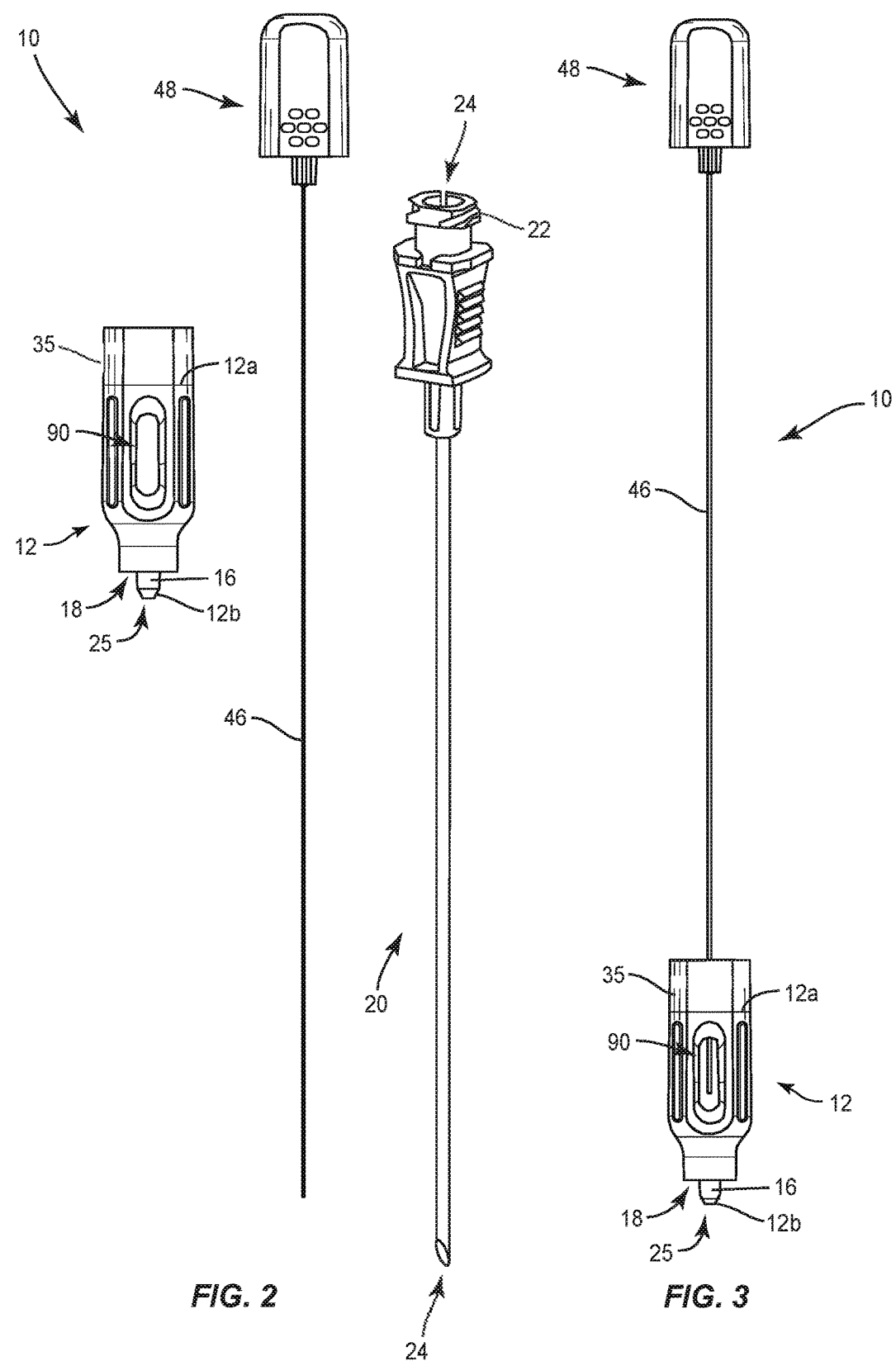
FIG. 2 is a front view of the drug pellet delivery system shown in FIG. 1, with parts separated.
FIG. 3 is a front view of the drug pellet delivery system shown in FIG. 1.

Cannula 20 includes a tip that is used to make an incision. Cannula 20 is then positioned through the incision such that the distal end of cannula 20 is positioned adjacent to the selected location to deliver one or more of the drug pellets to the selected location. As discussed above, cannula 20 may have a length that is sufficient to have at least a portion of housing 12 positioned above the incision when the distal end of cannula 20 is positioned adjacent to the selected location. Push rod 46 is positioned within cavity 40 and is moved relative to cartridge 26 and housing 12 in the direction shown by arrow A in FIG. 4 such that push rod 46 moves through opening 42 and into channel 44, as shown in FIG. 3. A medical practitioner can visually confirm that push rod 46 is positioned within channel 44 through window 90, as also shown in FIG. 3. Push rod 46 is advanced in the direction shown by arrow A in FIG. 4 until tip 46a of push rod 46 engages a proximal one of the drug pellets positioned in channel 44, as shown in FIG. 12. A medical practitioner can visually confirm that push rod 46 is engaging the drug pellets within channel 44 through window 90. Push rod 46 is further advanced in the direction shown by arrow A in FIG. 4 to push at least one of the drug pellets in channel 44 through lumen 52 and conduit 25 and into passageway 24 of cannula 20. The drug pellet(s) will move through passageway 24 to deliver the drug pellet to the selected target location for implantation within the patient.

Rails 56 and/or projection 72 maintain alignment of push rod 46 with channel 44 to block or redirect push rod 46 if push rod 46 is inserted into channel 44 in a direction that is transverse to the longitudinal axis defined by channel 44, as discussed herein. In particular, if push rod 46 be inserted through opening 42 and into channel 44 in a direction that is transverse (e.g., lateral) to the longitudinal axis defined by channel 44, the distal tip 46a of push rod 46 will engage the inner surface of one of portions 56b, as shown in FIG. 10. As push rod 46 moves within channel 44 in direction A shown FIG. 4, portions 56b will redirect push rod 46 between portions 56a such that push rod 46 is oriented parallel to the longitudinal axis defined by channel 44. Similarly, if push rod 46 be inserted through opening 42 and into channel 44 such that push rod 46 begins to lift out of channel 44, push rod will engage ramp 72a such that proximal end 82 of frame 80 deflects upwardly relative to middle portion 86 of frame 80 such that proximal end 82 extends transverse to middle portion 86. Tip 46a will slide along ramp 72a to guide push rod 46 into channel 44 such that push rod 46 is coaxial with channel 44.

Rails 58 and/or projection 76 maintain alignment of the drug pellets with channel 44 to block or redirect push the drug pellets if the drug pellets move laterally within channel 44, as discussed herein. In particular, if the drug pellets begin to move laterally within channel 44, the drug pellets will engage inner surfaces of rails 58 to redirect the drug pellets between rails 58 such that the drug pellets are positioned within channel 44. This maintains alignment of the drug pellets with channel 44 such that the drug pellets are aligned with lumen 52 such that push rod 46 can push the drug pellets through channel 44 and out of cartridge 26 through lumen 52. Similarly, if the drug pellets move within channel 44 such that the drug pellets begin to lift out of channel 44, the drug pellets will engage ramp 76a such that distal end 84 of frame 80 deflects upwardly relative to middle portion 86 of frame 80 such that distal end 84 extends transverse to middle portion 86, as shown in FIG. 12. The drug pellets will slide along ramp 76a to guide the drug pellets into channel 44 such that the drug pellets are coaxial with channel 44. This configuration allows push rod 46 to push the drug pellets through channel 44 and lumen 52 and into passageway 24 of cannula 20 without push rod 46 or the drug pellets becoming jammed within channel 44, as discussed herein.

In some embodiments, push rod 46 has a length that is long enough to adequately expel the drug depots through the combined length of housing 12, cartridge 26 and cannula 20. In some embodiments, push rod 46 has a length that is less than the combined length of housing 12 and cannula 20. That is, push rod 46 does not and cannot extend to or beyond the distal tip of cannula 20. In some embodiments, push rod 46 has a length that is greater than or equal to the combined length of housing 12, cartridge 26 and cannula 20 such that push rod 46 can be inserted into cartridge 26 and cannula 20 such that push rod 46 extends entirely through cannula 20. In some embodiments, push rod 46 has a length that is greater than the combined length of housing 12, cartridge 26 and cannula 20 such that push rod 46 can be inserted into cartridge 26 and through cannula 20 such that push rod 46 extends entirely through cannula 20 and out of an opening in a distal tip of cannula 20.

In some embodiments, a kit is provided that includes a plurality of push rods, such as, for example, push rods 46 that have different lengths and/or a plurality of cannulas, such as for example, cannula 20 that have different lengths. For example, in some embodiments, the kit includes a first push rod and a first cannula each having a length configured to deliver a drug depot into a petite patient, where the cannula does not need to penetrate deep into the patient. In some embodiments, the kit includes a second push rod and a second cannula, wherein at least one of the second push rod and the second cannula have a length that is greater than that of the first push rod and/or the first cannula such that the second push rod and the second cannula are configured to deliver a drug depot into a normal patient, where the second cannula needs to penetrate deeper into the patient, than with a petite patient. In some embodiments, the kit includes a third push rod and a third cannula, wherein at least one of the third push rod and the third cannula have a length that is greater than that of the second push rod and/or the second cannula such that the third push rod and the third cannula are configured to deliver a drug depot into an obese patient, where the third cannula needs to penetrate deeper into the patient, than with a normal patient. In some embodiments, the kit includes drug pellets, such as, for example, drug pellets 54 and other drug pellets discussed herein. In some embodiments, the kit includes a drug pellet delivery device, such as, for example a device having a housing (e.g., housing 12), a cartridge (e.g., cartridge 26), a ring 35 and a cover (e.g., cover 60) wherein the device is fully assembled in the kit. That is, the cover and the cartridge are fixed relative to one another and are positioned within a cavity in the housing such that the cartridge and cover are fixed relative to the housing, as discussed herein. In some embodiments, the drug pellets are pre-loaded into the cartridge. In some embodiments, the kit includes one or more cannula (e.g., cannula 20) and one or more plunger (e.g., plunger 48) that may be used in conjunction with the device. The cannula and/or the plunger may have different lengths and/or diameters, as discussed herein.

In some embodiments, at least one of the components of system 10 can be made of radiolucent materials such as polymers. In some embodiments, cannula 20 is made from a radio opaque material. Radiomarkers may be included for identification under x-ray, fluoroscopy, CT or other imaging techniques.

It is envisioned that the use of image guided technologies may be employed with the aid of the system 10. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A delivery device comprising:
 a housing comprising a cavity;
 a cartridge positioned within the cavity and comprising a body comprising an outer surface and having a concave inner surface extending into the body in a first direction and defining a channel having a longitudinal axis, the body comprising a first pair of rails protruding from the outer surface in a second direction opposite the first direction and a second pair of rails protruding from the outer surface in the second direction, wherein the first pair of rails is configured to block and redirect a plunger to maintain alignment of the plunger through the channel; and
 the plunger slidably disposed in the housing and the cartridge, the plunger being configured to move a drug depot through the channel and out of the housing,
 wherein the first pair of rails is spaced apart by the channel,
 wherein the first pair of rails is outward of the channel, and
 wherein each said rail of the first pair of rails comprises:
  a first planar surface parallel to the longitudinal axis of the channel; and
  a second planar surface tapered towards a distal end of the body.

2. The device as recited in claim 1, wherein the first pair of rails includes first and second rails that are spaced apart from one another by the channel.

3. The device as recited in claim 1, wherein the second pair of rails includes first and second rails that are spaced apart from one another by the channel.

4. The device as recited in claim 1, wherein the second pair of rails is configured to block and redirect the drug depot to maintain alignment of the drug depot through the channel.

5. The device as recited in claim 1, further comprising a cover removably attached to the cartridge.

6. The device as recited in claim 5, wherein the cover comprises a first projection positioned between the first pair of rails and a second projection positioned between the second pair of rails.

7. The device as recited in claim 5, wherein the cover includes a wall that is positioned over at least a portion of the channel.

8. The device as recited in claim 5, wherein the housing comprises a window and the cover is clear or translucent such that the drug depot within the channel would be visible through the window and the cover.

9. The device as recited in claim 5, wherein the cover includes tabs that are positioned within grooves of the body to attach the cover to the cartridge.

10. The device as recited in claim 1, wherein the body includes tabs that are positioned within openings in the housing to couple the cartridge to the housing.

11. The device as recited in claim 1, wherein the body includes a funnel portion positioned above the channel, the funnel portion comprising an opening that is in communication with the channel.

12. The device as recited in claim 1, wherein the housing comprises a passageway that is in communication with the channel such that the drug depot can be pushed through the channel with the plunger and exit the device through an opening at an end of the passageway.

13. The device as recited in claim 1, wherein the housing comprises a window positioned such that the drug depot within the channel would be visible through the window.

14. The device as recited in claim 1, wherein each said rail of the first pair of rails comprises:
a first portion parallel to a longitudinal axis of the channel; and
a second portion tapered towards a distal end of the body.

15. A kit comprising:
the device recited in claim 1; and
at least one drug depot configured to be positioned in the channel, the drug depot comprising a therapeutically effective amount of at least one drug and a biodegradable polymer.

16. A delivery device comprising:
a housing comprising a cavity;
a cartridge positioned within the cavity and comprising a body having an inner surface extending into the body, the inner surface defining a channel, the body comprising tabs that are positioned within openings in the housing to couple the cartridge to the housing, the body comprising a first pair of rails and a second pair of rails outward of the channel, the first pair of rails including first and second rails that are spaced apart from one another by the channel, the second pair of rails including third and fourth rails that are spaced apart from one another by the channel; and
a plunger slidably disposed in the housing and the cartridge, the plunger being configured to move a drug depot through the channel and out of the housing,
wherein the first pair of rails is configured to block and redirect the plunger to maintain alignment of the plunger through the channel, and
wherein the second pair of rails is configured to block and redirect the drug depot to maintain alignment of the drug depot through the channel.

17. The device as recited in claim 16, further comprising a cover removably attached to the cartridge.

18. The device as recited in claim 17, wherein the cover comprises a first projection positioned between the first pair of rails, a second projection positioned between the second pair of rails and a wall that is positioned over at least a portion of the channel.

19. The device as recited in claim 17, wherein the housing comprises a window and the cover is clear or translucent such that the drug depot within the channel would be visible through the window and the cover.

20. A delivery device comprising:
a housing comprising a cavity;
a cartridge positioned within the cavity and comprising a body having a channel at least partially defined by a recess in a surface, the body comprising a first pair of rails and a second pair of rails protruding from the surface, the first pair of rails including first and second rails that are spaced apart from one another by the channel, the second pair of rails including third and fourth rails that are spaced apart from one another by the channel;
a cover removably attached to the cartridge, the cover comprising a first projection positioned between the first pair of rails, a second projection positioned between the second pair of rails and a wall that is positioned over at least a portion of the channel and the first and second pairs of rails, the cover comprising tabs that are positioned within grooves of the body to attach the cover to the cartridge; and
a plunger slidably disposed in the housing and the cartridge, the plunger being configured to move a drug depot through the channel and out of the housing,
wherein the housing comprises a window and the cover is clear or translucent such that the drug depot within the channel would be visible through the window and the cover,
wherein the first pair of rails is configured to block and redirect the plunger to maintain alignment of the plunger through the channel, and
wherein the second pair of rails is configured to block and redirect the drug depot to maintain alignment of the drug depot through the channel.

* * * * *